US006848293B2

(12) United States Patent
DeRuiter et al.

(10) Patent No.: US 6,848,293 B2
(45) Date of Patent: Feb. 1, 2005

(54) WEIGHT DROP SYSTEM

(75) Inventors: Daniel A. DeRuiter, Kentwood, MI (US); Todd P. Collier, Saugatuck, MI (US); Daniel L. Brookhouse, Hudsonville, MI (US); Joel L. Mulder, Zeeland, MI (US); Michael J. Walcott, Hudsonville, MI (US); Ellis J. Gusky, New Boston, MI (US)

(73) Assignee: Johnson Controls Technology Company, Plymouth, MI (US)

( * ) Notice: Subject to any disclaimer, the term of this patent is extended or adjusted under 35 U.S.C. 154(b) by 0 days.

(21) Appl. No.: 10/227,604

(22) Filed: Aug. 23, 2002

(65) Prior Publication Data

US 2004/0035181 A1 Feb. 26, 2004

(51) Int. Cl.⁷ .................................................. G01M 7/00
(52) U.S. Cl. ...................................................... 73/12.13
(58) Field of Search ............................ 73/12.01, 12.09, 73/12.13, 12.03, 12.04, 12.05, 12.06, 12.07, 12.08, 12.11, 12.12

(56) References Cited

U.S. PATENT DOCUMENTS

| 652,391 | A | * | 6/1900 | Harris ......................... 122/327 |
| 3,566,668 | A | | 3/1971 | Browning et al. |
| 3,738,439 | A | | 6/1973 | Herbert |
| 4,006,626 | A | * | 2/1977 | Ruzicka et al. ............. 73/12.02 |
| 4,609,066 | A | * | 9/1986 | Layotte et al. ............... 181/121 |
| 4,766,965 | A | | 8/1988 | Luchinger |
| 4,991,472 | A | * | 2/1991 | Hollingsworth ............... 81/464 |
| 5,373,749 | A | | 12/1994 | Strand et al. |
| 5,457,984 | A | * | 10/1995 | Ambur et al. .............. 73/12.09 |
| 5,567,867 | A | | 10/1996 | Nazar |
| 5,786,526 | A | | 7/1998 | Byon |
| 5,824,880 | A | | 10/1998 | Burwell et al. |
| 6,023,984 | A | | 2/2000 | Mazur et al. |
| 6,035,728 | A | | 3/2000 | Jost |
| 6,224,519 | B1 | * | 5/2001 | Doolittle ....................... 482/98 |
| 6,242,820 | B1 | * | 6/2001 | Shankar et al. ............. 307/10.1 |
| 6,256,601 | B1 | | 7/2001 | Wipasuramonton et al. |

FOREIGN PATENT DOCUMENTS

DE 198 12 350 A1 10/1998

OTHER PUBLICATIONS

International Search Report for Application No. PCT/US 03/26275, received Dec. 22, 2003, 2 pages.

* cited by examiner

Primary Examiner—Max Noori
(74) Attorney, Agent, or Firm—Foley & Lardner LLP (57) ABSTRACT

A weight drop system includes a frame, a base weight, at least one supplemental weight, a carriage, at least one gripper carried by the carriage and a hold mechanism. The base weight is movable relative to the frame between an undeployed position and a deployed load applying position in which a load is applied. The at least one supplemental weight is actuatable between a load supplementing state in which the load being applied is increased and a non-supplementing state. The carriage moves between a raised position and a lowered retrieving position. The grippers move between a weight engaging position and a weight disengaging position. The hold mechanism holds at least the base weight in the undeployed position while the at least one gripper disengages or is disengaged from at least the base weight. Release of the base weight by the hold mechanism allows at least the base weight to fall to the load applying position.

72 Claims, 9 Drawing Sheets

WEIGHT DROP SYSTEM

FIELD OF THE INVENTION

The present invention generally relates to testing and calibration systems for repeatedly applying a load to an object or a series of objects. In particular, the present invention relates to a weight drop system for applying a load to an automotive component. Even more particular, the present invention relates to a weight drop system for dropping a weight upon a seat to be used in a transportation vehicle.

BACKGROUND OF THE INVENTION

Most modern vehicles today incorporate air bags and deployment systems. Weight drop systems are commonly employed in the automotive industry to apply a load to an automotive seat to test and calibrate air bag deployment systems. Such calibration and testing is necessary to ensure compliance with the federal motor vehicle safety standards (FMVSS). The deployment systems typically include various sensing systems, commonly known as PODS-B and Strain Gauge Occupancy sensing systems, incorporated into the automotive seat. The sensors identify the weight of the individual seated upon the seat. Based upon this sensed weight, the deployment system fires the air bag during a collision at a predetermined force. For example, such a deployment system may fire the air bag at full force for a full-sized adult but only fire the air bag at half force for a lighter adult or child. In such air bag and deployment systems, it is important that the sensors be properly calibrated and tested to accurately identify the weight of the seat occupant.

Various weight drop systems are commonly employed to drop a predetermined weight upon a vehicle seat to test and calibrate the sensors of the air bag deployment system. One known system includes a rigid rectangular frame including four linear round shafts which guide a single weight between a raised undeployed position and a deployed lowered position in which the weight applies a load to a seat. The weight is connected to a cable which is connected to a motorized winch. The motorized winch binds the cable to lift the weight to the raised position. To drop the weight, the winch is released from the cable so as to allow the weight in the cable to fall.

Although commonly employed, this known system has several drawbacks. Because the weight remains attached to the cable as the load is being applied, the inertia of the cable adds force above and beyond the calibrated weight, leading to a variance in the resulting load. In addition, the four round shafts used to guide the weight cause slight binding which introduces unwanted friction and load variations. As a result, calibration and testing accuracy is impaired. Furthermore, because the system only enables the use of a single weight, applying different weights or loads requires the redesign and modification of the system or requires the use of multiple systems to apply different loads.

SUMMARY OF THE INVENTION

According to one exemplary embodiment of the present invention, a weight drop system includes a frame, a base weight and at least one supplemental weight. The base weight is movable relative to the frame between an undeployed position and a deployed load applying position in which a load is applied. At least one supplemental weight is actuatable between a load supplementing state in which the load being applied is increased and a non-supplementing state.

According to yet another exemplary embodiment, the weight drop system includes a frame, a weight and an electromagnet. The weight is movable between an undeployed position and a deployed load applying position in which a load is applied. The electromagnet is coupled to the frame and is configured to releasably retain the weight in the undeployed position.

According to yet another exemplary embodiment, a weight drop system includes a frame and a weight. The weight is movable between an undeployed position and a deployed load applying position. The weight includes an elongate splined shaft slidably supported relative to the frame.

According to yet another exemplary embodiment, the weight drop system includes a frame and a weight retrieval system. The weight is movable between an undeployed position and a deployed load applying position. The weight retrieval system is configured to selectively engage and disengage the weight. The weight retrieval system is movable between a raised position and a lowered retrieving position.

According to yet another exemplary embodiment, the weight drop system includes a frame, a weight movable between a raised position and a lowered load applying position, engaging and lifting means and releasing means. The engaging and lifting means engage the weight and lift the weight from the lowered position to the raised position. The releasing means release the weight from the engaging and lifting means so that the weight falls to the lowered load applying position.

According to another exemplary embodiment, a method for dropping a load upon an object includes the steps of engaging a rigid weight, lifting the weight to a raised position and disengaging the weight such that the weight falls upon an object to apply a load to the object.

DETAILED DESCRIPTION OF THE PREFERRED EMBODIMENTS

Figure 1:
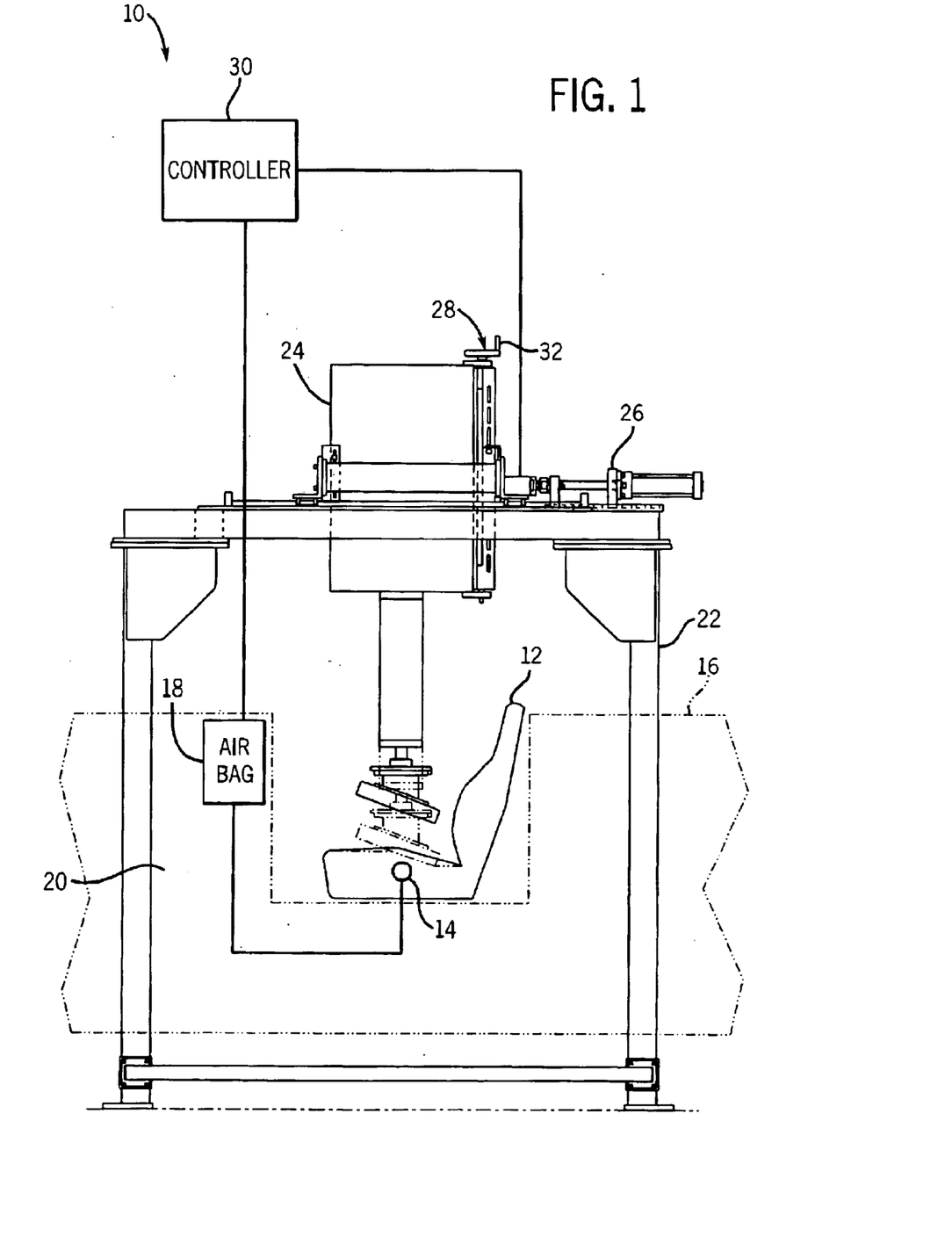
FIG. 1 is a side elevational view schematically illustrating a vehicle seat being tested or calibrated by an exemplary embodiment of a weight drop system of the present invention including a weight in a non-deployed position and a deployed load applying position (shown in phantom).
Figure 2:
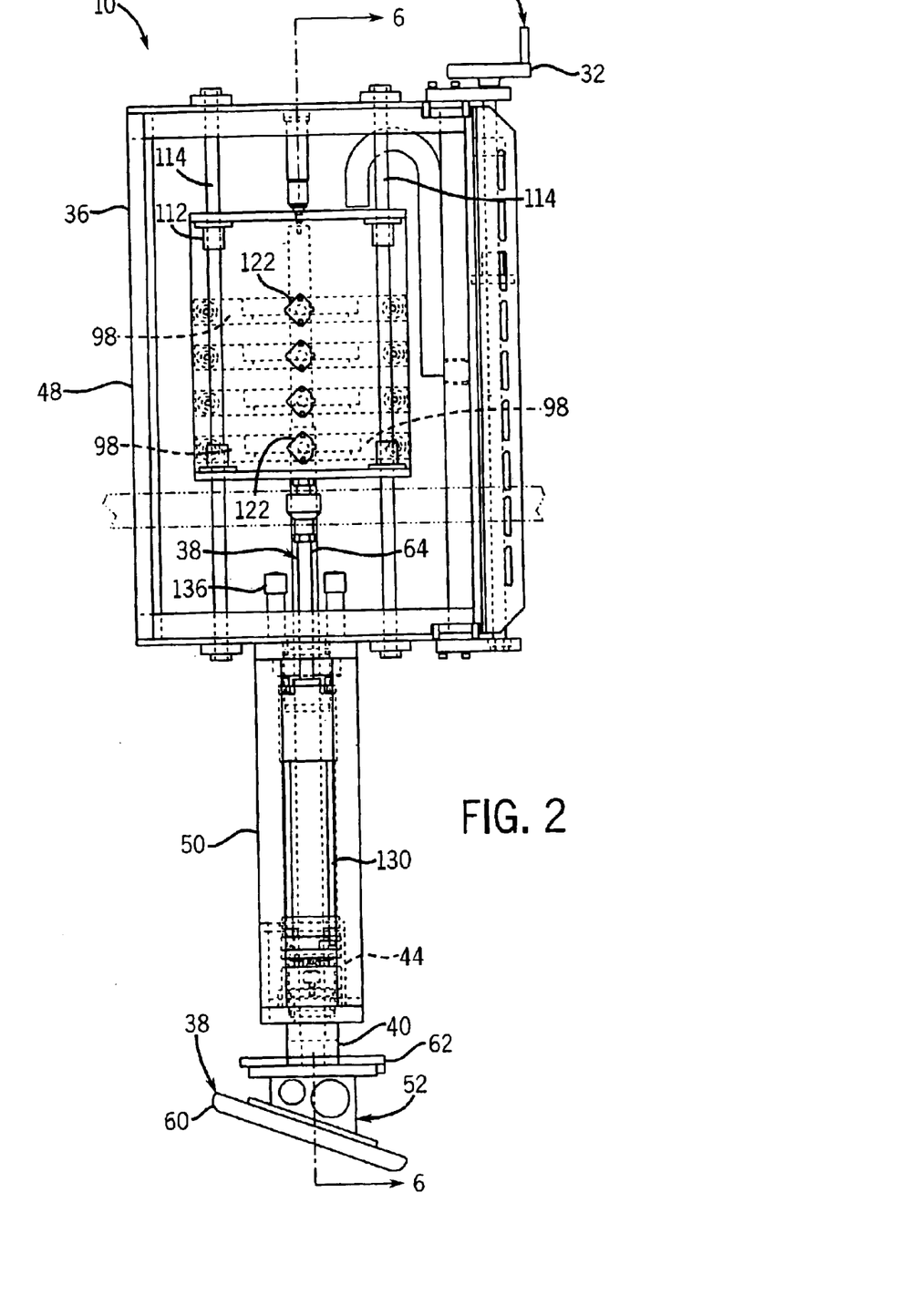
FIG. 2 is a side elevational view of a preferred embodiment of a weight drop subsystem of the system of FIG. 1.

FIG. 1 is a side elevational view schematically illustrating weight drop system 10 proximate an automotive seat 12 including a sensing system 14. Although sensing system 14 preferably comprises a conventionally known PODS-B sensor or a strain gauge occupancy sensing system configured to determine air bag deployment, sensing system 14 may comprise other conventionally known or future developed sensing systems associated with seat 12 for determining air bag deployment or for providing other presently known or future identified and needed functions which rely upon sensing a load or weight that is bearing upon an automotive seat or other component. Although seat 12 is illustrated as being tested while fully assembled and positioned within an automotive vehicle 16 (shown in phantom), weight drop system 10 may alternatively be employed with fully assembled seats not already mounted to an automotive vehicle or may be employed with particular seat components of unassembled seats. As shown in FIG. 1, automotive vehicle 16 includes an air bag 18 and a deployment controller 20. As conventionally known, deployment controller 20 receives signals from sensor 14 identifying a load placed upon seat 12. Based upon such signals, controller 20 generates control signals which control the force by which air bag 18 is deployed during a collision and other characteristics of the deployment of air bag 18. During calibration and testing, deployment controller 20 receives signals from sensor 14, wherein either or both of sensor 14 or deployment controller 20 are calibrated or adjusted as needed for accuracy.

Weight drop system 10 applies a pre-established or pre-determined load to sensor 14 to calibrate sensor 14 and/or controller 20. Preferably, system 10 applies a load to sensor 14 while sensor 14 is situated within seat 12. Although less desirable, in alternative applications, system 10 may apply a load directly to sensor 14. Weight drop system 10 generally includes main frame 22, weight drop subsystem 24, horizontal height adjustment mechanism 26, vertical height adjustment mechanism 28 and calibration/testing controller 30. Main frame 22 generally comprises a rigid structure configured to support subsystem 24 relative to sensor 14 and preferably seat 12. In the preferred embodiment illustrated, main frame 22 movably supports subsystem 24, enabling system 10 to be employed with sensors 14 associated with differently configured seats 12 and possibly differently configured vehicles 16. Although frame 22 is illustrated as extending from a floor, main frame 22 may alternatively be suspended from a ceiling or other structure.

Subsystem 24 is supported by main frame 22 and is configured to selectively apply at least one load to sensor 14. In the particular embodiment illustrated, subsystem 24 is configured to drop a weight under the force of gravity upon sensor 14. Subsystem 24 is also configured to retrieve the weight once the weight is dropped. Subsystem 24 is configured to release and drop the weight in a substantially frictionless manner without load variations as will be described in greater detail hereafter. As a result, testing and calibration accuracy is improved. Subsystem 24 is preferably also configured to selectively apply different loads to sensor 14. Although less desirable, subsystem 24 may alternatively be configured to apply only a single pre-established load.

Mechanisms 26 and 28 extend between main frame 22 and subsystem 24 and are configured to adjust the positioning of subsystem 24 relative to sensor 14 and seat 12. Mechanism 26 preferably comprises a linear actuator, such as a pneumatic cylinder assembly, configured to move subsystem 24 in a horizontal direction relative to frame 22 and an underlying seat 12. Although not shown, system 10 may additionally include an additional horizontal adjusting mechanism to move subsystem 24 in a horizontal direction perpendicular to the direction in which mechanism 26 moves subsystem 24. Mechanism 28 moves subsystem 24 in a vertical direction to adjust the distance by which the weight is dropped by subsystem 24. In the particular embodiment illustrated, mechanism 28 comprises a worm gear in engagement with a corresponding rack gear associated with main frame 22, wherein rotation of its hand crank 32 raises and lowers subsystem 24. In alternative embodiments, mechanisms 26 and 28 may comprise other manual or mechanisms powered by electrical, hydraulic, pneumatic or mechanical means.

Controller 30 comprises a control circuit operably coupled to sensor 14 either directly or indirectly. Controller 30 receives the signals from sensor 14 either directly or through controller 20 and analyzes such data to facilitate testing or calibration of sensor 14 and/or controller 20. In the particular embodiment illustrated, controller 30 also controls the operation of subsystem 24 and adjustment mechanism 26. As will be described in greater detail hereafter, controller 30 preferably controls the release and retrieval of the weight and receives data in verifying the weight being dropped. In the particular embodiment illustrated wherein subsystem 24 is configured to provide a plurality of different loads, controller 30 further controls the selection and retrieval of supplemental weights. In alternative applications, much of the automated control steps provided by controller 30 may be performed manually by the operator. Controller 30 also generates control signals for controlling adjustment mechanism 26 to move subsystem 24. In alternative applications where adjustment mechanism 28 comprises a powered actuator, controller 30 may also be configured to generate control signals in control of such an actuator.

FIGS. 2–7 illustrate weight drop subsystem 24 in greater detail. Weight drop subsystem 24 generally includes frame 36, weight 38, hold mechanism 40, weight retrieval system 42 and load verification sensor 44. Frame 36 generally comprises a rigid structure or framework supporting the remaining components of subsystem 24. Although frame 36 is illustrated as including an upper frame portion 48 and a lower frame portion 50, frame 36 may have any one of a variety of various sizes and configurations depending upon size and configuration of weight 38, hold mechanism 40, weight retrieval system 42, load verification sensor 44 and any other possible additional components.

Weight 38 generally comprises one or more units having a mass which when released by hold mechanism 40, fall under the force of gravity onto sensor 14 and seat 12. Weight 38 moves between a non-deployed raised position in which the weight is suspended above sensor 14 (shown in solid in FIG. 1) and a lowered deployed load applying position (shown in phantom in FIG. 1) in which the weight applies a load to sensor 14. In the particular embodiment illustrated,, the weight is preferably dropped a total distance, including seat penetration, of about seven inches. Weight 38 is movably supported relative to frame 36 so as to move and be guided between the two positions in a reliable, consistent and substantially frictionless manner.

In the particular embodiment illustrated, weight 38 generally includes a base weight 52 and supplemental weights 54, 56 and 58. Base weight 52 generally comprises a minimum amount of weight which may be applied by weight drop system 10. In the particular embodiment illustrated, base weight 52 has a weight of approximately 46 pounds. Depending upon the application, base weight 52 may have various other weight amounts. Base weight 52 generally includes contact portion 60, hold portion 62, shaft 64 and support portion 66. Contact portion 60 generally comprises the lowermost portion of base weight 52 which is configured to contact the cushion of seat 12. Contact portion 60 preferably comprises a circular disk. In alternative embodiments, contact portion 60 may comprise what is known as a b-form which simulates the butt of a seat occupant.

Hold portion 62 is coupled to contact portion 60 and provides an engagement surface 68 which faces upwardly and is adapted to be engaged by hold mechanism 40. For purposes of this disclosure, the term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature. As will be described in greater detail hereafter, hold mechanism 40 preferably comprises an electromagnet. Accordingly, at least portions of hold portion 62 preferably include a magnetic material which is capable of being attracted to an electromagnet. Although hold portion 62 is illustrated as comprising a plate, hold portion 62 may have various other structures or configurations.

Shaft 64 comprises an elongate rigid shaft extending from hold portion 62 to and beyond support 66. Shaft 64 slidably engages portions of frame 36 during movement of base weight 52 between the deployed and undeployed positions. In the particular embodiment illustrated, subsystem 24 includes bearings 70 coupled to frame 36 so as to slidably guide movement of shaft 64. Shaft 64 preferably comprises a splined shaft while bearings 70 comprise linear splined bearings. It is found that use of splined bearings provides the least amount of frictional resistance to provide sufficient guidance of shaft 64. Because shaft 64 is splined, shaft 64 resists undesirable rotation. Moreover, because movement of base weight 52 between the raised and lowered positions is guided substantially solely by the interaction with shaft 64, as compared to guidance provided by multiple shafts, frictional resistance and load variations are reduced. Although less desirable, base weight 52 may alternatively be guided by multiple shafts, may use other bearing configurations or shaft configurations.

Support portion 66 extends outwardly from shaft 64 and provides a platform upon which supplemental weights 54, 56 and 58 may be stacked if desired. In particular, support portion 66 has an upper surface 72 upon which supplemental weight 54 may rest. Support portion 66 has an opposite lower surface 74 which serves as an engagement surface adapted to be engaged by weight retrieval system 42 during retrieval of weight 38 and at times when weight 38 is in the raised position.

In the particular embodiment illustrated, support portion 66 comprises a pair of clamp weights configured as two semi-circular disks which fit together to form a complete circular disk and which extend into an annular groove 76 formed in shaft 64. In alternative applications, support 66 may be integrally formed with shaft 64 or may be permanently mounted to shaft 64 by various presently known or future developed connecting methods such as welding, bonding and the like.

Supplemental weights 54, 56 and 58 generally comprise additional mass which are configured to be selectively added to base weight 52 to increase the load being applied by weight drop system 10. In the particular embodiment illustrated, supplemental weights 54–58 enable the load to be increased from approximately 46 pounds to 220 pounds. Supplemental weights 54–58 each preferably has an identical bottom diameter and an identical top diameter regardless of whether the additional weight provided by supplemental weights 54, 56, 58 are identical or different than one another. Because the top diameter and bottom diameter of each of supplemental weights 54, 56, 58 are substantially the same diameter, engagement and disengagement of such weights by weight retrieval system 42 is facilitated.

Figure 7:
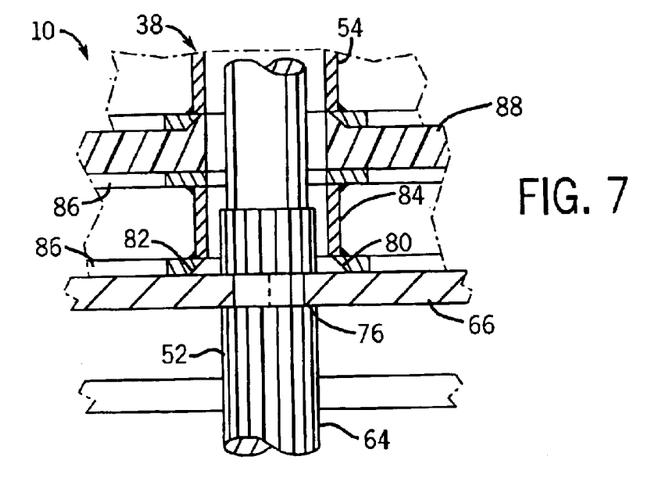
FIG. 7 is a fragmentary sectional view of the subsystem of FIG. 6 taken along line 7—7.

FIG. 7 illustrates support portion 66 and supplemental weights 54 and 56 in greater detail. As shown by FIG. 7, the upper surface of each of support portion 66 and supplemental weights 54, 56 and 58 are each provided with a frustro-conical surface 80 while each of the lower surfaces of supplemental weights 54, 56 and 58 are provided with a corresponding frustro-conical recess 82 configured to receive and mate with the frustro-conical projection. As a result, supplemental weight 54 mates with support portion 66 while supplemental weight 56 mates with supplemental weight 54 and so on. Such mating interaction retains supplemental weights 54, 56 and 58 relative to one another and relative to support portion 66 as weight 38 is dropped.

As further shown by FIG. 7, each of supplemental weights 54, 56 and 58 has a general wagon-wheel configuration with an annular hub 84 extending between solid or perforated disks 86. The extent to which disks 86 are solid or imperforate and the extent to which there is a gap between disk 86 is largely determined by the desired amount of additional weight to be provided by the particular supplemental weight. As further shown by FIG. 7, each supplemental weight 54, 56, 58 additionally includes an upper insulating member 88, preferably formed from rubber or plastic. Member 88 provides surface 80 on supplemental weights 54, 56, 58.

When weight 38 is in the raised position, shaft 64 of base weight 52 projects through hubs 84. At the same time, supplemental weights 54, 56, 58 are in abutting relationship with one another and with support portion 66. When weight 38 is released by hold mechanism 40, base weight 52 and any supplemental weights 54, 56, 58 released by weight retrieval system 42 fall together to apply a load to the underlying seat.

Hold mechanism 40 is coupled to frame 36 and is configured to releasably retain at least base weight 52 in a non-deployed raised position. Preferably, hold mechanism 40 is configured to hold at least base weight 52 in the raised position even while weight retrieval system 42 is completely disengaged from weight 38. In the particular embodiment illustrated, hold mechanism 40 comprises at least one electromagnet 59 having a lower hold surface 90 extending above and opposite to engagement surface 68 of hold portion 62 of base weight 52. Hold mechanism 40 magnetically attracts and holds weight 38 in the raised position or alternatively allows weight 38 to fall. This release is achieved in a substantially frictionless manner. Preferably, controller 30 (shown in FIG. 1) includes an electromagnet controller that has one adjustment interface. This adjustment interface (a dial) controls the duration and amplitude of a reverse pulse DC current that is sent to the magnets 59 to cancel the magnetic field in the magnets 59. This causes a clean and quick release of the weight. In an alternative embodiment, the electromagnet controller for hold mechanism 40 is distinct from controller 30.

The operation of hold mechanism 40 is as follows. Controller 30 causes a sustained signal to be sent to the electromagnet controller which tells the electromagnet controller to turn on the magnets 59. 2) When this signal is removed, the electromagnet controller reverses the polarity (DC current) to the magnets 59 for a duration set by the adjustment dial. After the end of the reversal pulse, the magnets 59 remain de-energized until the magnet controller receives an energization signal to energize the magnets 59.

Although hold mechanism 40 is illustrated as being coupled to frame 36 via load verification sensor 44, hold mechanism 40 may alternatively be directly coupled to frame 36 in those applications where load verification sensor 44 is omitted. Furthermore, although less desirable, in alternative embodiments, base weight 52 may be provided with at least one electromagnet opposite a magnet attractive plate coupled to frame 36. In yet other alternative embodiments, various other mechanisms may be utilized to releasably hold or retain base weight 52 in the raised position while at the same time permitting quick and substantially frictionless release of the weight 38. In such an application, the engagement surface of base weight 52 should preferably extend below or to a side of the hold surface of hold mechanism 40 to permit frictionless release.

Figure 6:
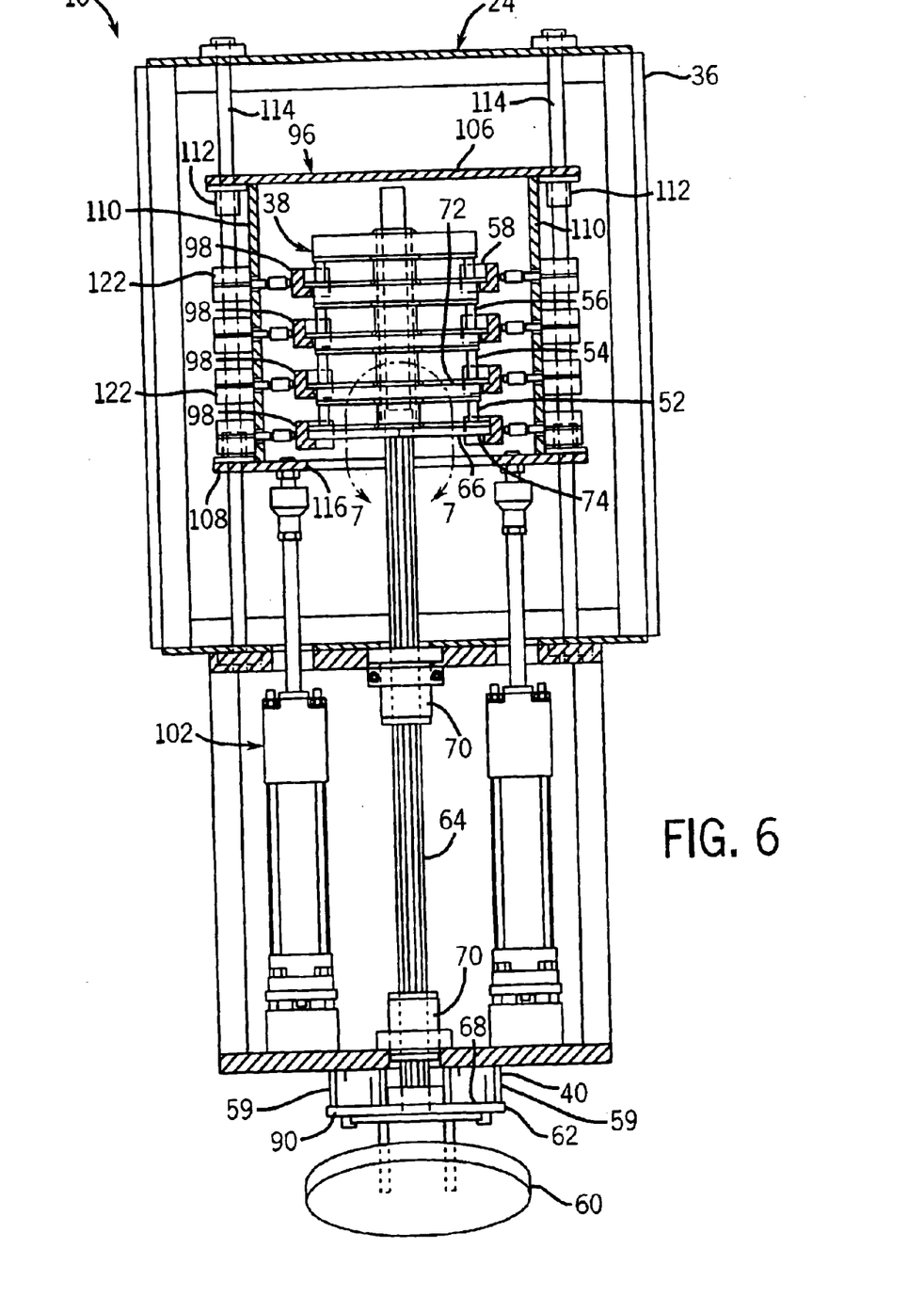
FIG. 6 is a front elevational view schematically illustrating the subsystem of FIGS. 1–5 with the grippers in engagement with the weight, with a carriage carrying the grippers in a raised position and with a hold mechanism further retaining the weight in the raised position.

Weight retrieval system 42 is coupled to the frame and is configured to selectively engage and disengage at least base weight 52 and to lift at least base weight 52 from the lower deployed position to the raised position. In embodiments where weight drop system 10 includes supplemental weights 54, 56, 58, weight retrieval system 42 is also configured to selectively add or remove supplemental weights 54, 56, 58 from the load being applied by weight 38. Weight retrieval system 42 generally includes carriage 96, grippers 98, gripper sensors 100 and carriage positioning system 102. Carriage 96 generally comprises a structure which is vertically movable relative to frame 36 between a raised position in which weight 38 is suspended at least in part by hold mechanism 40 and a lower weight retrieving position in which the dropped weights may be engaged for retrieval. Although carriage 96 may have a variety of different shapes and configurations, the preferred embodiment of carriage 96 is best shown in FIG. 6. The preferred embodiment of carriage 96 includes a rigid framework formed by a top plate 106, a bottom plate 108 and a pair of end plates 110. Top plate 106 and bottom plate 108 are coupled to one another by end plates 110 and are movably supported relative to frame 36 by bearings 112 which slidably support carriage 96 along a plurality of guide shafts 114 coupled to frame 36. Bottom plate 108 includes an opening 116 shaped and dimensioned to allow support portion 66 of base weight 52 and supplemental weights 54, 56 and 58 to pass therethrough. End plates 110 support grippers 98 and sensors 100.

Figure 4:
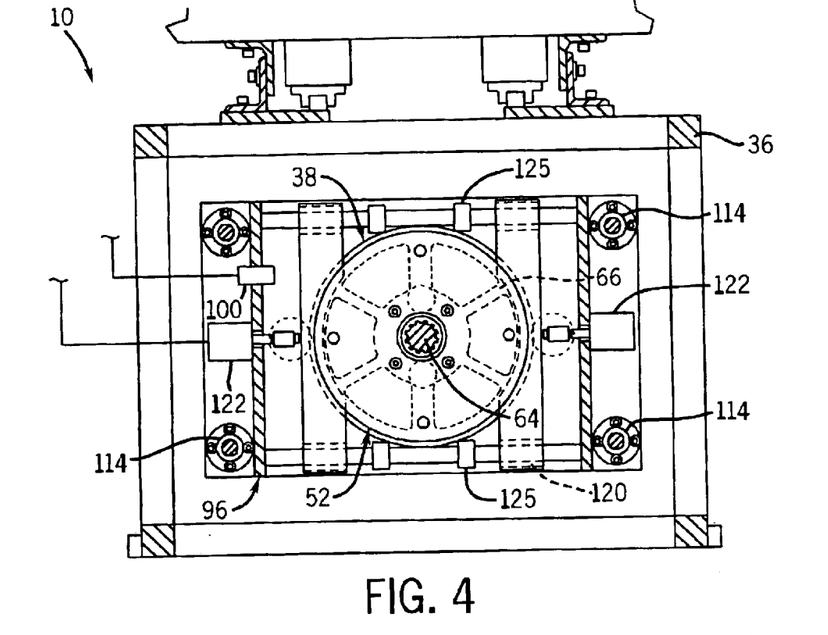
FIG. 4 is a sectional view of the subsystem of FIG. 3 taken along line 4—4, illustrating grippers in engagement with a weight.
Figure 5:
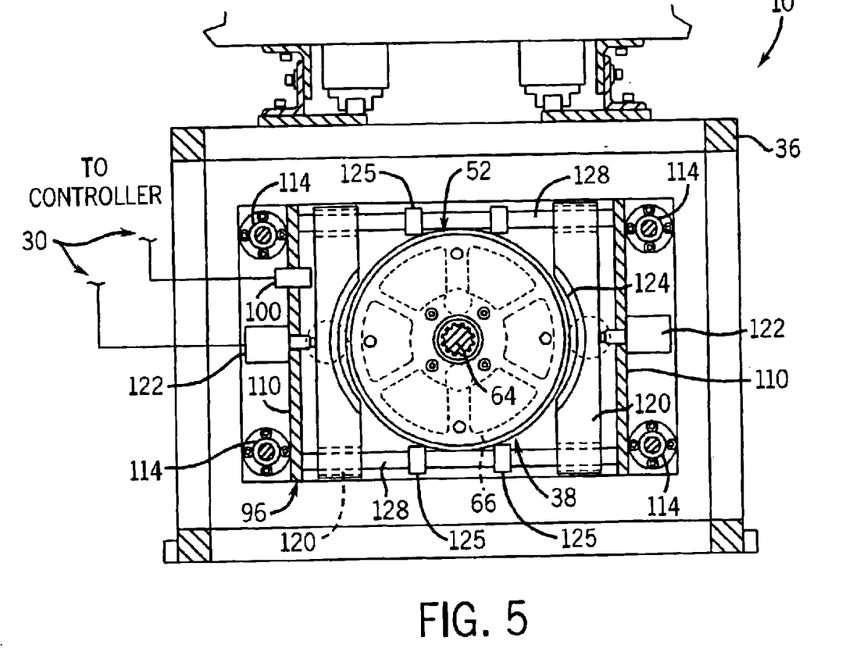
FIG. 5 illustrates the subsystem of FIG. 4 with the grippers disengaged from the weight.

Grippers 98 are coupled to and are carried by carriage 96 and are configured to move between a weight engaged position (shown in FIG. 4) and an outward weight disengaged position (shown in FIG. 5). In the weight engaged position, grippers 98 retain a corresponding one of weights 52, 54, 56 or 58 relative to carriage 96. In the engaged position, grippers 98 engage weights 52, 54, 56 and 58 such that as carriage 96 is moved from the lowered retrieving position to the raised position, the weights 52, 54, 56 and 58 are also elevated to the raised position. In the weight disengaged position, grippers 98 allow their respective weights 52, 54, 56 and 58 to move relative to carriage 96 and to move below the grippers. In the disengaged position, grippers 98 permit their respective weights to fall under the force of gravity and apply a load to seat 12 upon the release of base weight 52 by hold mechanism 40.

FIGS. 4 and 5 best illustrate a preferred embodiment of one of grippers 98. Each gripper 98 preferably includes a gripper bar 120 and an actuator 122. Bar 120 comprises an elongate bar extending on one side of weight 38 and includes an arcuate cutout 124 which substantially parallels the outer circumference of weights 52, 54, 56 and 58. To prevent wearing of the gripper faces from rubbing against the weights, shaft collars 125 are used to prevent grippers 98 from clamping on the weights 52, 54, 56 and 58. A clearance of about 0.01 inches to about 0.03 inches between the face of the gripper 98 and the weights 52, 54, 56 and 58 is established using such shaft collars.

Bars 120 move between the weight engaged position and the weight disengaged position relative to carriage 96. In the embodiment illustrated, bars 120 move along guide shafts 128 which extend between end plates 110.

Actuators 122 move gripper bars 120 between the engaged and disengaged positions. Actuators 122 preferably comprise pneumatic cylinders coupled between bars 120 and end plates 110. Although actuators 122 are illustrated as comprising pneumatic cylinders, actuators 122 may alternatively comprise various other known actuators configured to move one object relative to another object whether by electrical (e.g. solenoid), pneumatic, hydraulic or other mechanical means. Although less desirable, actuators 122 may be replaced by manual movement means. Furthermore, in lieu of comprising bars which slide along guide shafts, grippers 98 may have any of a variety of other configurations and shapes and may be movably supported relative to carriage 96 in various other fashions. As clear from the present disclosure, the number of grippers 98 carried by carriage 96 may be varied depending upon the number, if any, of supplemental weights that are provided to vary the load potentially applied by weight drop system 10.

Sensors 100 (schematically shown in only FIGS. 4 and 5) comprise conventionally known or future developed sensing devices configured to detect the presence of weights 52, 54, 56, 58 within their respective grippers 98. Sensors 100 generate signals representing the presence of the weights supported by gripper 98 and transmit such signals to controller 30 to assist in the control of weight retrieval system 42. In the preferred embodiment, sensors 100 comprise teachable photo eyes. Alternatively, such sensors may comprise other known or future developed sensing devices. Furthermore, in lieu of sensing the presence of weights at a particular gripper 98, sensors 100 may be configured to sense the position of gripper 98. As best shown by FIGS. 4 and 5, a pair of opposite grippers 98 are provided for each of weights 52, 54, 56 and 58. For each pair of opposing grippers, weight retrieval system 42 includes a sensor 100. In lieu of utilizing a pair of opposing grippers 98 for each weight, weight retrieval system 42 may alternatively utilize a single gripper 98, either as illustrated or in an alternative configuration.

Figure 3:
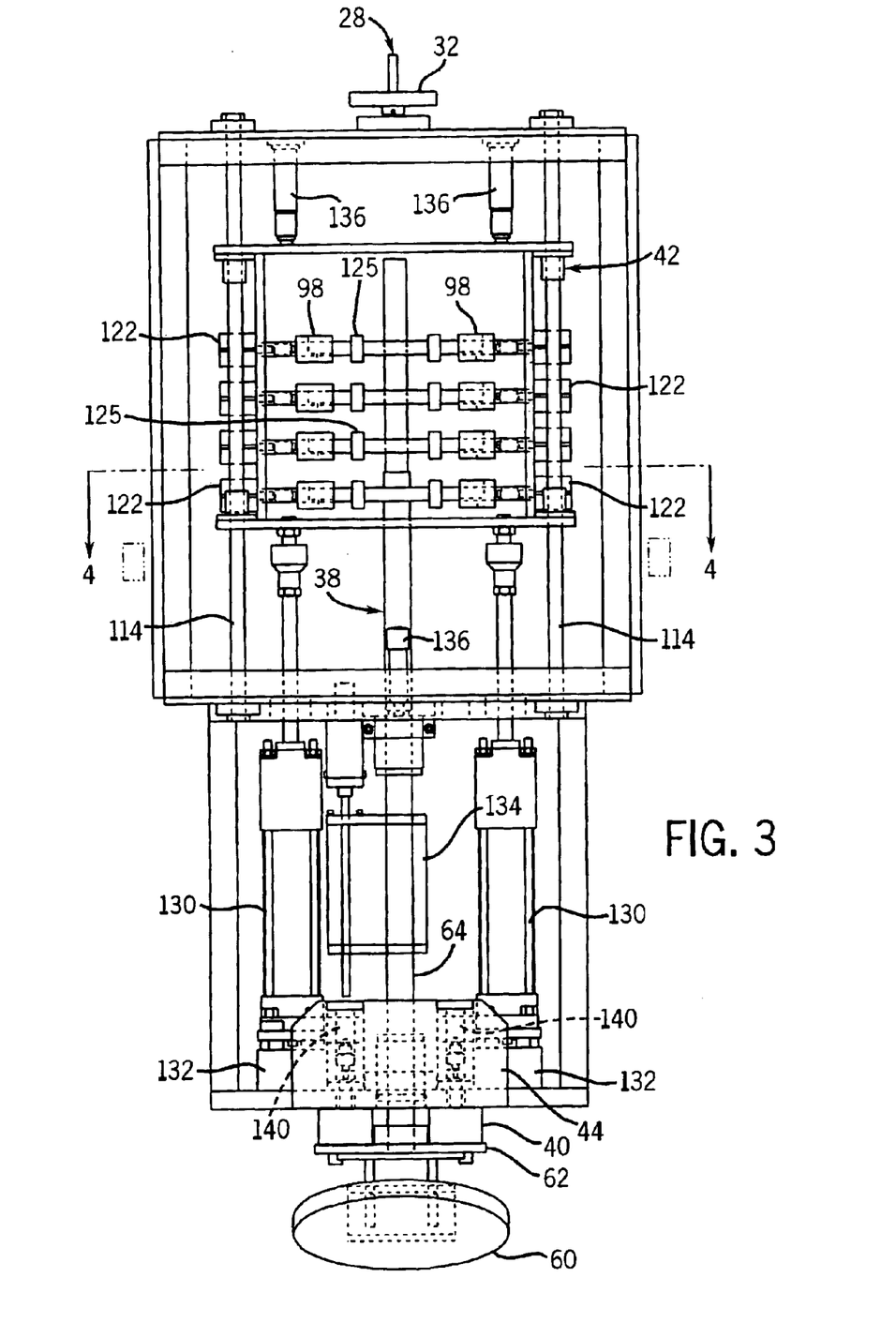
FIG. 3 is a front elevational view of the weight drop subsystem of FIG. 2.

FIG. 3 best illustrates carriage positioning system 102. Carriage positioning system 102 is configured to move carriage 96 between the raised position shown in FIG. 3 and the lowered weight retrieving position. In the particular embodiment illustrated, weight positioning system 102 is also configured to move carriage 96 to at least one intermediate position between the raised position and the lowered weight retrieving position. Carriage positioning system 102 generally includes main actuators 130, supplemental actuators 132, weight position sensor 134 and optional shocks 136. Actuators 130 and 132 are coupled together in series and cooperate with one another to move carriage 96 between the raised position, the lowered weight retrieving position and at least one intermediate position. In the particular embodiment illustrated, actuators 130 and 132 are supported by frame 36 below carriage 96 and comprise pneumatic cylinder assemblies. Main actuator 130 preferably comprises a 63 mm bore by eight inch stroke locking cylinder while actuator 132 preferably comprises an 80 mm bore by 10 mm stroke compact cylinder. When carriage 96 is in the fully raised position, actuators 130 and 132 are all in the extended position. To lower carriage 96 to the lowered weight retrieving position, actuators 130 are retracted while actuators 132 remain extended. To lower carriage 96 from the raised position to an intermediate position, only actuators 132 are retracted. This results in carriage 96 being lowered by approximately ⅛ of an inch. As will be described in greater detail hereafter, lowering carriage 96 to the intermediate position while hold mechanism 40 holds base weight 52 and any added supplemental weights 54, 56, 58, results in grippers 98 being lowered out of engagement with their respective weights, allowing grippers 98 to be moved outwardly to the disengaged position without wearing against the overlying weights. Once at least the lowermost gripper 98 and selected additional grippers 98 are moved outwardly to the disengaged position, those disengaged weights may be dropped by release of base weight 52 by hold mechanism 40.

Although actuators 130 and 132 are illustrated as preferably comprising pneumatic cylinders, actuators 130 and 132 may comprise various other conventionally known or future developed linear actuators powered under pneumatic, electrical, hydraulic or mechanical means. Although positioning system 102 is illustrated as including actuators 130 and 132 coupled in series, positioning system 102 may alternatively utilize single actuators or actuators coupled to carriage 96 in parallel. Although actuators 130 and 132 are illustrated as extending below carriage 96, actuators 130 and 132 may alternatively be positioned above carriage 96. Various means for moving carriage 96 are contemplated. For example, guide shafts 114 may alternatively threadably engage carriage 96, wherein powered rotation of one or more of shafts 114 raises and lowers carriage 96.

Sensor 134 is configured to generate signals representing the relative position of base weight 52. Such signals are transmitted to controller 30 which uses such signals to control actuators 130, 132, actuators 122 and hold mechanism 40, all of which are operably coupled to controller 30 (shown in FIG. 1). In the particular embodiment illustrated, sensor 134 comprises a linear position transducer coupled to frame 36 and positioned proximate to shaft 64 of base weight 52. Alternatively, sensor 134 may comprise various other known sensing devices such as photo eyes and the like. Sensor 134 enables controller 30 to accurately control the remaining components of weight drop system 10 despite different possible positions of weight 38 after being dropped due to seat variations.

Shocks 136 are coupled to frame 36 above and below carriage 96. Shocks 136 absorb extra force resulting from excess movement of carriage 96. In alternative embodiments, shocks 136 may additionally be provided with limit sensors coupled to controller 30 to further identify the position of carriage 96.

Load verification sensor 44 is configured to verify the amount of weight or load being dropped by system 10. Load verification sensor 44 comprises a load cell assembly having a pair of conventionally known load cells 140 coupled between frame 36 and hold mechanism 40 such that the weight engaging portions of hold mechanism 40 are solely suspended from frame 36 via the load cells 140. As a result, upon disengagement of grippers 98 from the weights to be dropped, the entire weight of the weights to be dropped is supported by hold mechanism 40 and is transmitted through the load cells 140. The load cells 140 generate signals representative of the sensed weight. Such signals are transmitted to controller 30 to verify the precise weight being dropped by system 10. In alternative embodiments, various other load verification systems may be employed.

Figure 8:
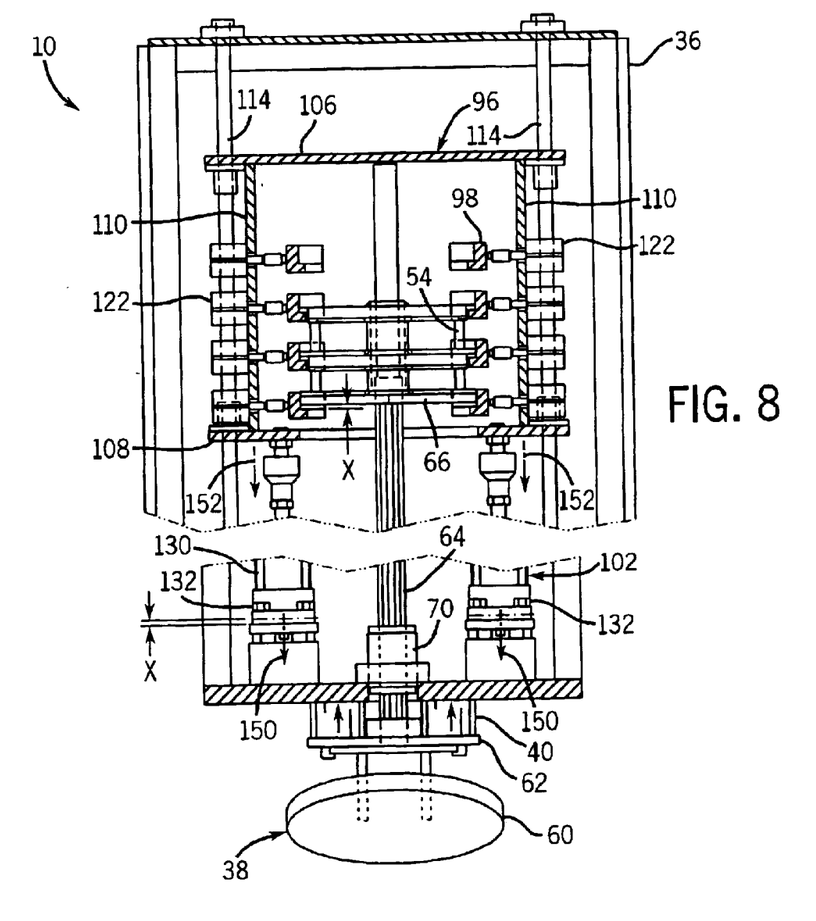
FIG. 8 illustrates the subsystem of FIG. 6 with the carriage in an intermediate position while the hold mechanism retains the weight in the raised position.

FIGS. 8–12 illustrate a weight drop cycle of system 10. FIG. 8 illustrates carriage 96 in a fully raised position with each of grippers 98 in the inwardly positioned inward engaged positions. For ease of illustration, only base weight 52 and one supplemental weight 54 are shown. Once a seat enters a test station and the sensor 14 of the seat 12 is connected to controller 30 (shown in FIG. 1), the cycle is initiated by controller 30. In particular, controller 30 generates control signals which are transmitted to actuators 132 and which cause actuators 132 to retract in the direction indicated by arrows 150 by a distance of X (nominally ⅛ of an inch). As a result, carriage 96 is lowered in the direction indicated by arrows 152 which also causes grippers 98 to be lowered by a distance of X. At the same time, current is supplied to the electromagnets of hold mechanism 40 such that base weight 52 and each of the supplemental weights 54, 56 and 58 remain in the raised position.

Figure 9:
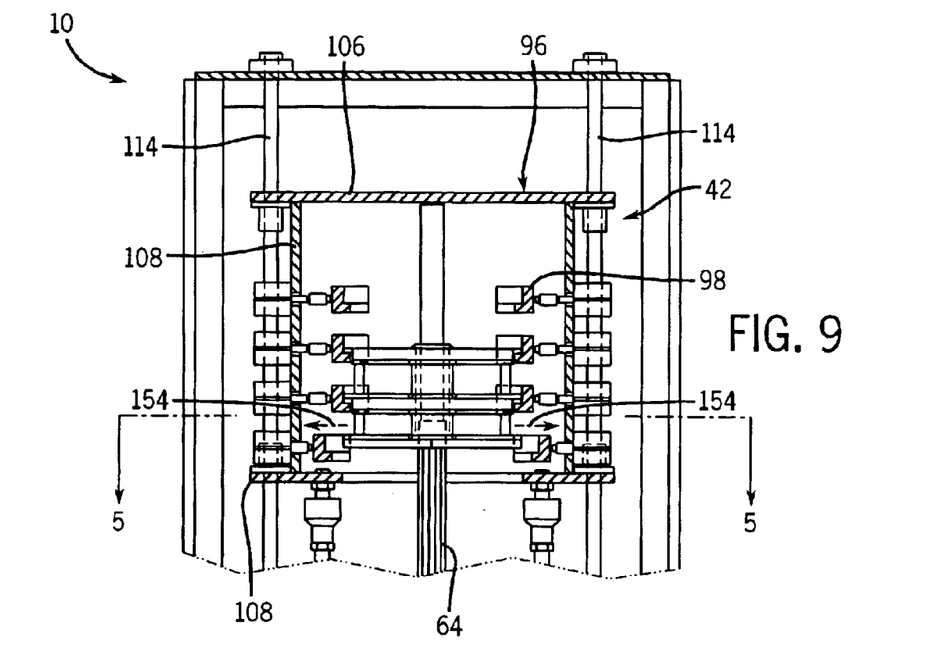
FIG. 9 is a fragmentary view of the subsystem of FIG. 6 further illustrating disengagement of a lowermost set of grippers from a base weight.

FIG. 9 illustrates the circumstance in which only the base weight 52 is to be dropped. Accordingly, as shown in FIG. 9, only the lowermost gripper 98 is moved outwardly from the inward engaged position to the outward disengaged position as indicated by arrows 154. Because the lowermost gripper 98 is lowered and spaced below support portion 66 of base weight 52, lowermost gripper 98 may be moved to the disengaged position without any frictional engagement with support portion 66 of base weight 52. Sensors 100 generate signals indicating the removal of base weight 52 from the lowermost gripper 98. Such signals are submitted to controller 30. Once the lowermost gripper 98 is in the disengaged position, as detected by sensor 100, controller 30 generates control signals which are transmitted to actuator 132 causing actuator 132 to once again extend so as to elevate carriage 96 until supplemental weights 54, 56 and 58 are supported by their respective grippers and lifted slightly above support portion 66 of base weight 52. the removal of base weight 52 from the lowermost gripper 98. Such signals are submitted to controller 30. Once the lowermost gripper 98 is in the disengaged position, as detected by sensor 100, controller 30 generates control signals which are transmitted to actuator 134 causing actuator 134 to once again extend so as to elevate carriage 96 until supplemental weights 54, 56 and 58 are supported by their respective grippers and lifted slightly above support portion 66 of base weight 52.

At this point in time, the entire weight of base weight 52, alone, is passed through load verification sensor 44. Load verification sensor 44 generates signals representative of the weight of the weight about to be dropped, base weight 52, and transmits such signals to controller 30. This data is recorded.

Figure 11:
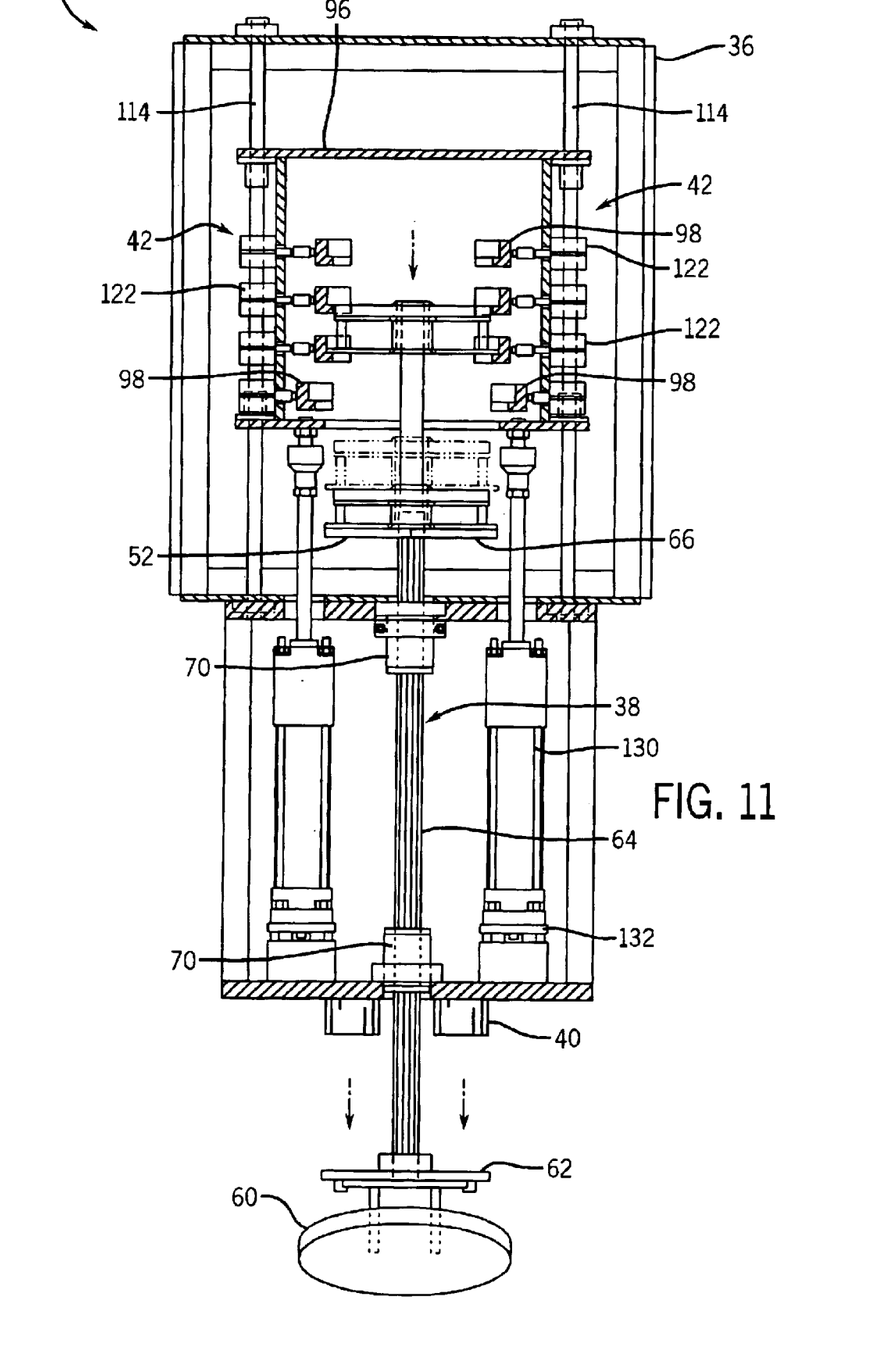
FIG. 11 illustrates the subsystem of FIG. 9 upon release of the hold mechanism to drop the weight.

Controller 30 generates a control signal which is transmitted to hold mechanism 40. In the particular embodiment illustrated, this signal cessates the supply of current to the electromagnets of hold mechanism 40, allowing base weight 52 to freely drop. Data from sensor 14 is then gathered and recorded by controller 30 or an alternative recording device. The dropping of base weight 52 is shown in FIG. 11.

Figure 12:
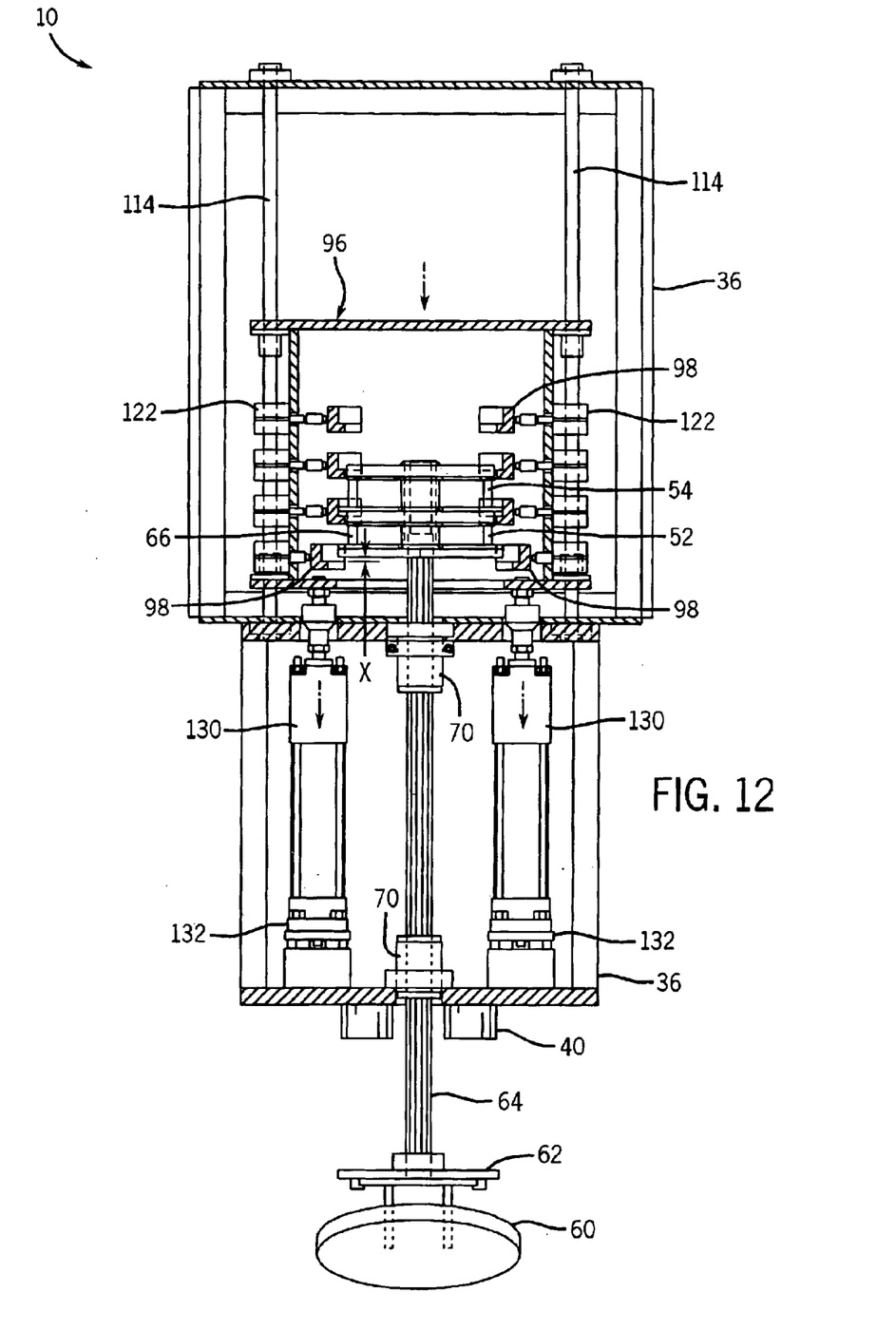
FIG. 12 illustrates the subsystem of FIG. 11 with the carriage moved to a lowered retrieving position prior to movement of the first set of grippers to the engaged position and further movement of the carriage and engaged weight to the raised position.

As shown by FIG. 12, once the weight is dropped, and the seat data is recorded, controller 30 generates control signals which are transmitted to actuators 130 to retract, lowering carriage 96 to the lowered retrieval position in which the lowermost gripper 98 extends at least partially below support portion 66 of base weight 52. Once carriage 96 has been sufficiently lowered as determined by controller 30 based upon signals from sensor 130, controller 30 generates control signals which are transmitted to actuator 122 of the lowermost gripper 98 causing the lowermost grippers 98 to move inwardly to the engaged position. Once the lowermost gripper 98 is in the engaged position, controller 30 generates control signals which are transmitted to actuators 130 which causes actuators 130 to extend and to lift carriage 96 and the lowermost grippers into underlying engagement with support portion 66 of base weight 52. Continued extension of actuators 130 raises base weight 52 to the raised position.

Once base weight 52 is in the completely raised position, controller 30 generates a control signal which is transmitted to hold mechanism 40. In the preferred embodiment, the control signal re-energizes the electromagnets of hold mechanism 40 to hold base weight 52 in position. The cycle may then be repeated for another seat or a repeated testing of the same seat.

Figure 10:
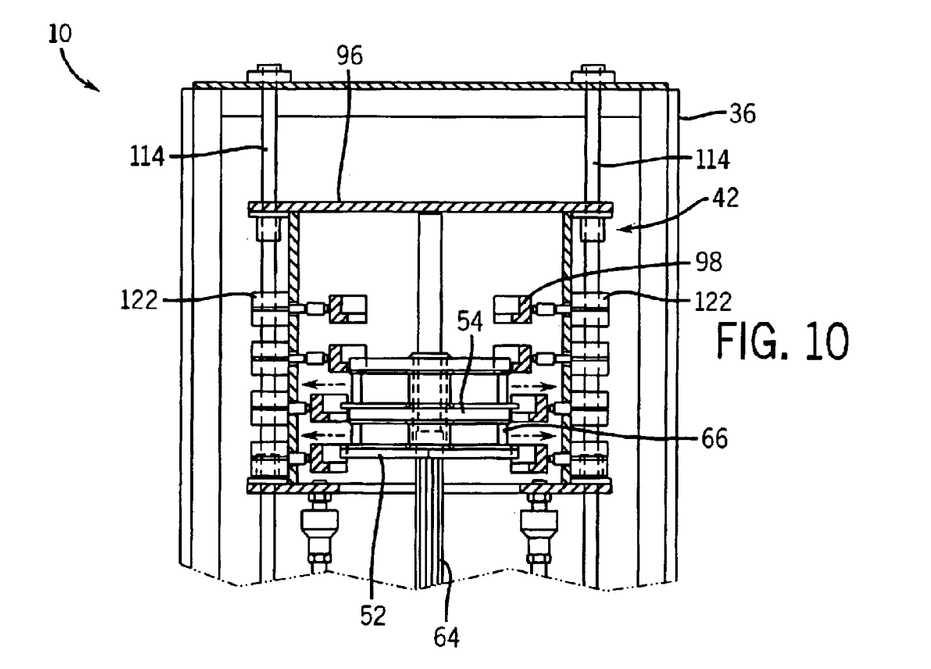
FIG. 10 is a fragmentary view of the subsystem of FIG. 9 further illustrating disengagement of a second set of grippers from a supplemental weight.

FIG. 10 illustrates a step from the same cycle described above except for the addition of supplemental weight 54 to the load being dropped. In contrast to the step shown in FIG. 9, the step shown in FIG. 10 additionally involves the retraction of the grippers 98 corresponding to supplemental weight 54 outwardly to the disengaged position. As a result, the entire weight of supplemental weight 54 rests upon the support portion 66 of base weight 52 and will be dropped with base weight 52.

Overall, weight drop system 10 enables one or more weights to repeatedly be dropped in a substantially frictionless manner during a testing or calibration procedure. Weight drop system 10 also enables the load being dropped to be varied without requiring disassembly or modification of the machine. Such benefits are achieved in part by various features of weight drop system 10. Such features include the use of a single splined shaft for guiding movement of the weight, the use of the hold mechanism that engages the weight above or to a side of the weight to facilitate frictionless release, the specific use of an electromagnet to release the weight, the lowering of the gripper out of frictional contact with the weight prior to movement of the gripper to the disengaged position and prior to release of the weight, the selection of different weight combinations by grippers 98, and the uniform sizes of the weights. Additional benefits are also obtained as a result of the load verification sensor, the preferred embodiment of the positioning system 102 and employment of sensors 122 and 44 which facilitate automation, calibration or testing verification and manufacturing efficiencies. Although the combination of such structures and features provides synergistic benefits in the preferred embodiment, such features may alternatively be employed independent of one another in alternative embodiments of weight drop system 10. In addition to testing and calibrating air bag deployment sensing systems, weight drop system 10 may be modified for various other testing or calibration applications in both automotive and non-automotive applications.

Although the present invention has been described with reference to preferred embodiments, workers skilled in the art will recognize that changes may be made in form and detail without departing from the spirit and scope of the invention. For example, although different preferred embodiments may have been described as including one or more features providing one or more benefits, it is contemplated that the described features may be interchanged with one another or alternatively be combined with one another in the described preferred embodiments or in other alternative embodiments. The system 10 includes several features in combination with one another which may be employed independently of one another depending on the particular application. Because the technology of the present invention is relatively complex, not all changes in the technology are foreseeable. The present invention described with reference to the preferred embodiments and set forth in the above definitions is manifestly intended to be as broad as possible. For example, unless specifically otherwise noted, the definitions reciting a single particular element also encompass a plurality of such particular elements.

What is claimed is:

1. A weight drop system comprising:
   a frame;
   a base weight movable relative to the frame between an undeployed position and a deployed load applying position in which a load is applied; and
   at least one supplemental weight actuatable between a load supplementing state in which the load being applied is increased and a supplementing state, wherein the at least one supplemental weight rests upon a portion of the base weight when in the weight force supplementing state and wherein the at least one supplemental weight is suspended and spaced above the base weight when in the non-supplementing state.

2. The system of claim 1 including at least one sensor configured to sense a first position of the base weight while the base weight is in contact with a target at a first height and a second distinct position of the base weight while the base weight is in contact with a target at a second height.

3. The system of claim 1, including at least one gripper coupled to the frame, wherein the at least one gripper moves between an engaged position in which at least one supplemental weight is suspended in the non-supplementing state and a disengaged position in which the at least one supplemental weight is in the weight force supplementing state.

4. The system of claim 3, including at least one actuator for moving the at least one gripper between the engaged position and the disengaged position.

5. The system of claim 1, including a weight retrieval system configured to selectively engage and disengage at least the base weight and to lift at least the base weight to a raised position.

6. The system of claim 5, wherein the weight retrieval system includes:
   a carriage movable between the raised position and a lowered retrieving position; and
   a carriage positioning system configured to stationarily support the carriage in the raised position without operator assistance.

7. The system of claim 6, wherein the carriage positioning system includes at least one non-human powered linear actuator configured to move the carriage between raised and lowered positions.

8. The system of claim 6, wherein the carriage is movable to at least one intermediate position between the raised position and the lowered retrieving position and wherein the carriage positioning system is configured to releasably retain the carriage in the at least one intermediate position without operator assistance.

9. The system of claim 8, including a hold mechanism configured to releasably retain at least the base weight in the non-deployed position when the carriage is in the at least one intermediate position.

10. The system of claim 9, wherein the hold mechanism includes at least one electromagnet.

11. The system of claim 8, including two linear actuators connected in series between the carriage and the frame, wherein selective extension and retraction of the two linear actuators moves the carriage between the raised position, the lowered position and the at least one intermediate position.

12. The system of claim 6, wherein the weight retrieval system includes at least one gripper carried by the carriage and movable between an engaged position in which the at least one supplemental weight is suspended in the non-supplementing state and a disengaged position in which the at least one supplemental weight is in the weight force supplementing state.

13. The system of claim 5 wherein the weight retrieval system includes at least one gripper movable between an engaged position in which at least one supplemental weight is suspended in the non-supplementing state and a disengaged position in which the at least one supplemental weight is in the weight force supplementing state.

14. The system of claim 1, wherein the base weight includes an elongate splined shaft slidably supported relative to the frame.

15. The system of claim 14, wherein movement of the base weight between the undeployed position and the deployed position is guided exclusively by interaction with the splined shaft.

16. The system of claim 1, including a plurality of linear actuators coupled in a series, the plurality of linear actuators configured to move at least the base weight between the undeployed position and the deployed position.

17. The system of claim 1, including at least one sensor configured to sense positioning of the base weight.

18. The system of claim 1, including at least one load sensor configured to sense the weight force of the base weight while in the undeployed position and any supplemental weight in the weight force supplementing state.

19. The system of claim 1, including an electromagnet coupled to the frame and configured to releasably retain the base weight in the undeployed position.

20. The system of claim 19, wherein the electromagnet is stationarily coupled to the frame as the base weight is moved from the deployed weight force applying position to the undeployed position.

21. The system of claim 19, wherein the base weight extends above the electromagnet when the base weight is in the deployed weight force applying position.

22. The system of claim 3, wherein the at least one gripper moves horizontally between the engaged position and the disengaged position.

23. The system of claim 3 including at least one sensor configured to detect the presence of at least one supplemental weight of the at least one supplemental weight in engagement with the at least one gripper.

24. The system of claim 1 including:
a hold mechanism configured to releasably retain the base weight in the undeployed position; and
a weight force verification sensor coupled between the frame and the hold mechanism, wherein the weight force to be applied by the base weight and any supplemental weight in the weight force supplementing state is transmitted to the frame through the weight force verification sensor while the base weight is in the undeployed position and wherein the weight force verification sensor is configured to sense the weight force to be applied by the base weight and any supplemental weight in the weight force supplementing state while the base weight is in the undeployed position.

25. The system of claim 1, wherein the base weight is movable relative to the frame and is configured to strike a target distinct from the system.

26. The system of claim 25, wherein the base weight is configured to strike the target while the target is at a first height relative to the frame or while the target is at a second distinct height relative to the frame.

27. A weight drop system comprising:
a frame;
a weight movable between an undeployed position and a deployed weight force applying position in which a weight force is applied;
an electromagnet coupled to the frame and configured to releasably retain the weight in the undeployed position; and
a carriage configured to selectively engage and disengage the weight, wherein the carriage is movable between a raised position and a lowered retrieving position along a vertical axis, wherein the carriage is movable relative to the electromagnet.

28. The system of claim 27, wherein the weight includes:
a base weight; and
at least one supplemental weight actuatable between a weight force supplementing state in which the weight force being applied is increased and a non-supplementing state.

29. The system of claim 27, wherein the weight includes an elongate splined shaft slidably supported relative to the frame.

30. The system of claim 27, including at least one gripper carried by the carriage and at least one actuator coupled to the at least one gripper, wherein the at least one actuator moves the at least one gripper between a weight engaged position and a weight disengaged position.

31. The system of claim 27, including:
at least one gripper; and
at least one actuator coupled to the at least one gripper, wherein the at least one actuator moves the at least one gripper between a weight engaged position and a weight disengaged position.

32. The system of claim 27, wherein the electromagnet is stationarily coupled to the frame.

33. The system of claim 27, wherein the weight extends above the electromagnet when the weight is in the deployed load applying position.

34. The system of claim 27, wherein the weight interacts with the frame along an extension of a only single shaft during movement from the undeployed position to the deployed load applying position.

35. The system of claim 30, wherein the at least one gripper moves horizontally between the engaged position and the disengaged position.

36. The system of claim 27 including:
   a hold mechanism configured to releasably retain the weight in the undeployed position; and
   a weight force verification sensor coupled between the frame and the hold mechanism, wherein the weight force to be applied by the weight and any supplemental weight in the weight force supplementing state is transmitted to the frame through the weight force verification sensor while the weight is in the undeployed position and wherein the weight force verification sensor is configured to sense the weight force to be applied by the weight and any supplemental weight in the weight force supplementing state while the weight is in the undeployed position.

37. The system of claim 27, wherein the base weight is movable relative to the frame and is configured to strike a target distinct from the system.

38. The system of claim 37, wherein the base weight is configured to strike the target while the target is at a first height relative to the frame or while the target is at a second distinct height relative to the frame.

39. The system of claim 27 including at least one sensor configured to sense a first position of the base weight while the base weight is in contact with a target at a first height and a second distinct position of the base weight while the base weight is in contact with a target at a second height.

40. A weight drop system comprising:
   a frame;
   a weight movable between an undeployed position and a deployed load applying position, the weight including an elongate splined shaft slidably supported relative to the frame, wherein the base weight is movable relative to the frame and is configured to strike a target distinct from the system.

41. The system of claim 40 including:
   a hold mechanism configured to releasably retain the base weight in the undeployed position; and
   a weight force verification sensor coupled between the frame and the hold mechanism, wherein the weight force to be applied by the base weight and any supplemental
   weight in the weight force supplementing state is transmitted to the frame through the weight force verification sensor while the base weight is in the undeployed position and wherein the weight force verification sensor is configured to sense the weight force to be applied by the base weight and any supplemental weight in the weight force supplementing state while the base weight is in the undeployed position.

42. The system of claim 40 including at least one sensor configured to sense a first position of the base weight while the base weight is in contact with a target at a first height and a second distinct position of the base weight while the base weight is in contact with a target at a second height.

43. The system of claim 40 including a weight retrieval system configured to selectively engage and disengage the weight, wherein the weight retrieval system is movable between a raised position and a lowered retrieving position.

44. A weight drop system for use with an automotive component, the system comprising:
   a frame configured to extend proximate the automotive component;
   a weight movable between an undeployed position and a deployed weight force applying position in which a load is applied to the automotive component; and
   weight retrieval system configured to selectively engage and disengage the weight, wherein the weight retrieval system is movable between a raised position and a lowered retrieving position; and
   a hold mechanism configured to releasably retain the weight in the non-deployed position when the weight retrieval system is disengaged from the weight.

45. The system of claim 44, including an electromagnet coupled to the frame and configured to releasably retain the base weight in the undelayed position.

46. The system of claim 44, wherein the electromagnet is stationarily coupled to the frame as the base weight is moved from the deployed weight force applying position to the undeployed position.

47. The system of claim 45, wherein the base weight extends above the electromagnet when the base weight is in the deployed weight force applying position.

48. The system of claim 44, wherein the weight interacts with the frame along an extension of a single shaft during movement from the undeployed position to the deployed load applying position.

49. The system of claim wherein 44, the base weight is movable relative to the frame and is configured to strike a target distinct from the system.

50. The system of claim 44 including at least one sensor configured to sense a first position of the base weight while the base weight is in contact with a target at a first height and a second distinct position of the base weight while the base weight is in contact with a target at a second height.

51. A weight drop system for use with an automotive component, the system comprising:
   a frame configured to extend proximate the automotive component;
   a weight movable between a raised position and a lowered weight force applying position in which a load is applied to the automotive component;
   means for engaging the weight and lifting the weight along a vertical axis from the lowered position to the raised position; and
   means for releasing the weight from the engaging and lifting means and from all other external tethers so that the weight falls to the lowered load applying position.

52. The system of claim 51, wherein the means for releasing the weight is configured to release the weight from the engaging and lifting means in a frictionless manner.

53. A method for dropping a load upon an automotive component, the method comprising:
   engaging a rigid weight;
   lifting the weight to a raised position along a vertical axis; and
   disengaging the weight such that the weight falls upon an automotive component to apply a weight force to the automotive component, wherein disengagement of the weight is frictionless.

54. The method of claim 53, wherein the weight includes at least one engagement surface, wherein the at least one engagement surface is engaged by a hold surface to support the weight above the object and wherein the hold surface is above or to a side of the engagement surface prior to disengagement.

55. The method of claim 53, wherein the weight includes first and second engagement surfaces, wherein the weight is engaged at the first engagement surface by a lift surface extending below the first engagement surface during lifting of the weight and wherein the weight is engaged at the second engagement surface by a hold surface extending above the second engagement surface.

56. The method of claim 55, wherein the lift surface is disengaged from the first engagement surface prior to disengagement of the hold surface and the second engagement surface, wherein disengagement of the hold surface permits the weight to fall upon the automotive component below.

57. The method of claim 53, including sensing the load of the weight prior to disengagement of the weight.

58. The method of claim 53, wherein the automotive component includes a sensor, wherein the sensor senses a weight force applied to the automotive component by the weight.

59. The method of claim 53, wherein the automotive component comprises a vehicle seat.

60. A weight drop system comprising:
a frame;
a weight movable relative to the frame between an undeployed position and a deployed weight force applying position in which a weight force is applied;
a weight retrieval system configured to selectively engage and disengage at least the base weight and to lift at base weight to a raised position, wherein the weight retrieval system includes a carriage movable between the raised position and a lowered retrieving position, wherein the weight retrieval system includes a carriage position system including at least one linear actuator configured to move the carriage between the raised and lowered positions, wherein the carriage is movable to at least one intermediate position between the raised position and the lowered retrieving position; and
a hold mechanism configured to releasably retain at least the base weight in the non-deployed position when the carnage is in the at least one intermediate position.

61. A weight drop system comprising:
a frame;
a weight movable relative to the frame between an undeployed position and a deployed weight force applying position in which a weight force is applied;
a weight retrieval system configured to selectively engage and disengage at least the base weight and to lift at least the base weight to a raised position, wherein the weight retrieval system includes a carriage movable between the raised position and a lowered retrieving position, wherein the weight retrieval system includes a carriage position system including two linear actuators connected in a series between the carriage and the frame, wherein selected extension or retraction of the two linear actuators moves the carriage between the raised position and the lowered position.

62. A method for dropping a load upon an automotive component, the method comprising:
engaging a rigid weight;
lifting the weight to a raised position; and
disengaging the weight such that the weight falls upon an automotive component to apply a load to the automotive component, wherein the weight includes at least one engagement surface, wherein the at least one engagement surface is engaged by a hold surface to support the weight above the object and wherein the hold surface is above or to a side of the engagement surface prior to disengagement.

63. A method for dropping a load upon an automotive component, the method comprising:
engaging a rigid weight;
lifting the weight to a raised position; and
disengaging the weight such that the weight falls upon an automotive component to apply a load to the automotive component, wherein the weight includes first and second engagement surfaces, wherein the weight is engaged at the first engagement surface by a lift surface extending below the first engagement surface during lifting of the weight and wherein the weight is engaged at the second engagement surface by a hold surface extending above the second engagement surface.

64. A method for dropping a load upon an automotive component, the method comprising:
engaging a rigid weight;
lifting the weight to a raised position;
disengaging the weight such that the weight falls upon an automotive component to apply a load to the automotive component; and
sensing the load of the weight prior to disengagement of the weight.

65. A weight drop system comprising:
a frame;
a weight movable between an undeployed position and a deployed weight force applying position in which a weight force is applied;
an electromagnet configured to releasably retain the weight in the undeployed position; and
a load verification sensor coupled between the frame and the electromagnet, wherein the weight force to be applied is transmitted to the frame through the load verification sensor while the weight is in the undeployed position and wherein the load verification sensor is configured to sense the weight force to be applied by the weight while the weight is in the undeployed position.

66. A weight drop system comprising:
a frame;
a base weight movable relative to the frame between an undeployed position and a deployed weight force applying position in which a weight force is applied, wherein the base weight is movable relative to the frame and is configured to strike a target distinct from the system; and
at least one supplemental weight actuatable between a weight force supplementing state in which the weight force being applied is increased and a non-supplementing state.

67. A weight drop system comprising:
a frame;
a base weight movable relative to the frame between an undeployed position and a deployed weight force applying position in which a weight force is applied;
at least one supplemental weight actuatable between a weight force supplementing state in which the weight force being applied is increased and a non-supplementing state; and
a weight retrieval system configured to selectively engage and disengage at least the base weight and to lift at least the base weight to a raised position, wherein the weight retrieval system includes:
a carriage movable between the raised position and a lowered retrieving position; and
a carriage positioning system configured to stationarily support the carriage in the raised position without operator assistance.

68. The system of claim 67, wherein the carriage positioning system includes at least one non-human powered linear actuator configured to move the carriage between the raised and lowered positions.

69. The system of claim 67, wherein the carriage is movable to at least one intermediate position between the raised position and the lowered retrieving position and wherein the carriage positioning system is configured to releasably retain the carriage in the at least one intermediate position without operator assistance.

70. A weight drop system comprising:

a frame;

a base weight movable relative to the frame between an undeployed position and a deployed weight force applying position in which a weight force is applied;

at least one supplemental weight actuatable between a weight force supplementing state in which the weight force being applied is increased and a non-supplementing state, wherein the at least one supplemental weight rests upon a portion of the base weight when in the weight force supplementing state; and at least one gripper coupled to the frame, wherein the at least one gripper moves between an engaged position in which at least one supplemental weight is suspended in the non-supplementing state and a disengaged position in which the at least one supplemental weight is in the weight force supplementing state.

71. A weight drop system comprising:

a frame;

a base weight movable relative to the frame between an undeployed position and a deployed weight force applying position in which a weight force is applied;

at least one supplemental weight actuatable between a weight force supplementing state in which the weight force being applied is increased and a non-supplementing state; and at least one sensor configured to sense positioning of the base weight.

72. A weight drop system comprising:

a frame;

a base weight movable relative to the frame between an undeployed position and a deployed weight force applying position in which a weight force is applied;

at least one supplemental weight actuatable between a weight force supplementing state in which the weight force being applied is increased and a non-supplementing state; and an electromagnet coupled to the frame and configured to releasably retain the base weight in the undeployed position, wherein the electromagnet is stationarily coupled to the frame as the base weight is moved from the deployed weight force applying position to the undeployed position.

* * * * *